US008437876B2

(12) United States Patent
Receveur et al.

(10) Patent No.: US 8,437,876 B2
(45) Date of Patent: May 7, 2013

(54) PATIENT HEALTH BASED SUPPORT APPARATUS CONFIGURATION

(75) Inventors: Timothy J. Receveur, Guilford, IN (US); Stephen C. Flint, Fortville, IN (US); Charles A. Lachenbruch, Summerville, SC (US)

(73) Assignee: Hill-Rom Services, Inc., Batesville, IN (US)

( * ) Notice: Subject to any disclaimer, the term of this patent is extended or adjusted under 35 U.S.C. 154(b) by 661 days.

(21) Appl. No.: 12/537,839

(22) Filed: Aug. 7, 2009

(65) Prior Publication Data

US 2011/0035057 A1    Feb. 10, 2011

(51) Int. Cl.
*A61G 5/00* (2006.01)
*A61G 1/003* (2006.01)
*A61G 1/00* (2006.01)
*G01M 1/38* (2006.01)
*G05D 16/00* (2006.01)
*H01H 43/00* (2006.01)
*A47B 71/00* (2006.01)

(52) U.S. Cl.
USPC .......... 700/275; 5/81.1 R; 5/81.1 C; 5/81.1 T; 5/600; 700/301; 700/302; 700/306

(58) Field of Classification Search .................. 5/81.1 R, 5/81.1 C, 81.1 T, 600; 700/275, 301, 302, 700/306
See application file for complete search history.

(56) References Cited

U.S. PATENT DOCUMENTS

| | | | | |
|---|---|---|---|---|
| 3,742,527 A * | 7/1973 | Johnston et al. | | 5/611 |
| 4,631,767 A * | 12/1986 | Carr et al. | | 5/714 |
| 4,738,264 A * | 4/1988 | Orlando | | 600/484 |
| 4,934,468 A * | 6/1990 | Koerber et al. | | 177/144 |
| 5,561,412 A | 10/1996 | Novak et al. | | |
| 5,592,374 A * | 1/1997 | Fellegara et al. | | 705/3 |
| 5,630,238 A * | 5/1997 | Weismiller et al. | | 5/600 |
| 5,647,079 A * | 7/1997 | Hakamiun et al. | | 5/713 |
| 5,699,038 A | 12/1997 | Ulrich et al. | | |
| 5,715,548 A | 2/1998 | Weismiller et al. | | |
| 5,745,937 A * | 5/1998 | Weismiller et al. | | 5/624 |
| 5,781,949 A * | 7/1998 | Weismiller et al. | | 5/715 |
| 5,930,152 A * | 7/1999 | Dumont et al. | | 700/302 |
| 6,468,237 B1 * | 10/2002 | Lina | | 601/150 |
| 7,038,588 B2 | 5/2006 | Boone et al. | | |
| 7,092,376 B2 | 8/2006 | Schuman | | |
| 7,154,397 B2 | 12/2006 | Zerhusen et al. | | |
| 7,253,366 B2 | 8/2007 | Bhai | | |
| 7,296,312 B2 | 11/2007 | Menkedick et al. | | |
| 7,315,535 B2 | 1/2008 | Schuman | | |

(Continued)

OTHER PUBLICATIONS

Virone et al., "An Advanced Wireless Sensor Network for Health Monitoring", IEEE, 2006, 4 pages.*

(Continued)

*Primary Examiner* — Charles Kasenge
*Assistant Examiner* — Thomas Stevens
(74) *Attorney, Agent, or Firm* — Barnes & Thornburg LLP

(57) ABSTRACT

A person-support apparatus operates according to a set of default operating parameters, processes information corresponding to an occupant of the person-support apparatus from a receiver to determine if an optimal value for an operating parameter is different from the default value, modifies a default operating parameter to an optimal value based on the information corresponding to the occupant of the person-support apparatus to create a modified operating parameter, and operates the person-support apparatus utilizing the modified operating parameter.

26 Claims, 6 Drawing Sheets

U.S. PATENT DOCUMENTS

| | | | |
|---|---|---|---|
| 7,319,386 B2 | 1/2008 | Collins, Jr. et al. | |
| 7,480,951 B2* | 1/2009 | Weismiller et al. | 5/600 |
| 7,487,562 B2 | 2/2009 | Frondorf et al. | |
| 7,746,218 B2* | 6/2010 | Collins et al. | 340/286.07 |
| 7,861,334 B2* | 1/2011 | Lemire et al. | 5/53.1 |
| 7,962,981 B2* | 6/2011 | Lemire et al. | 5/616 |
| 7,975,335 B2* | 7/2011 | O'Keefe et al. | 5/616 |
| 2002/0014951 A1 | 2/2002 | Kramer et al. | |
| 2003/0052787 A1* | 3/2003 | Zerhusen et al. | 340/573.1 |
| 2006/0049936 A1* | 3/2006 | Collins et al. | 340/539.11 |
| 2007/0004971 A1* | 1/2007 | Riley et al. | 600/300 |
| 2007/0157385 A1* | 7/2007 | Lemire et al. | 5/600 |
| 2008/0028533 A1 | 2/2008 | Stacy et al. | |
| 2008/0094207 A1 | 4/2008 | Collins, Jr. et al. | |
| 2008/0097733 A1 | 4/2008 | Alsafadi | |
| 2008/0109255 A1 | 5/2008 | Allen et al. | |
| 2008/0235872 A1* | 10/2008 | Newkirk et al. | 5/600 |
| 2009/0100599 A1* | 4/2009 | Rawls-Meehan | 5/616 |
| 2009/0217460 A1 | 9/2009 | Bobey et al. | |
| 2010/0212087 A1* | 8/2010 | Leib et al. | 5/81.1 R |

OTHER PUBLICATIONS

Tanimoto et al, "Measurement of SCI Patient's Buttock Pressure on Wheelchair and Bed", IEEE, 2001, 5 pages.*

Hu et al., "Congestion-Aware, Loss-Resilient Bio-Monitoring Sensor Networking for Mobile Health Applications", IEEE 2009, p. 450-465.*

Yonezawa et al., "A New Intelligent Bed Care System for Hospital and Home Patients", Biomedical Instrumentation & Technology, 2005, 7 pages.*

Fisher, Andrea R., et al., "Factors Associated with Pressure Ulcers in Adults in Acute Care Hospitals", *Advances in Skin & Wound Care*, vol. 17, No. 2, pp. 80-90.

* cited by examiner

PATIENT HEALTH BASED SUPPORT APPARATUS CONFIGURATION

BACKGROUND OF THE INVENTION

The present disclosure is related to the configuration of the operating parameters of a person-support apparatus. More specifically, the present disclosure is related to the automatic configuration of a person-support apparatus based on health parameters of a particular patient.

Person-support apparatuses are known to include various operational functions including bed movement functions, environmental controls such as controls for lighting and television, and nurse call functionality. In addition, various operating parameters related to the delivery of care to the patient may be varied or the operation may be limited. For example, bed exit monitoring, control of therapeutic devices such as a therapy mattress or other therapy devices may include parameters which are controlled based on characteristics of the patient supported on the apparatus, such as the patient's weight, for example.

With regard to bed exit monitoring, various levels of detection may be selected depending on various risk factors for the patient. In addition, in particular situations, bed movement functions may be limited to reduce risk of injury to a patient. For example, patients who require traction should not be subjected to bed movement. It has been known to employ bed movement lockouts to limit the operation of the person-support apparatus.

Generally, a caregiver considers various risk factors and adjusts the operating parameters of a particular person-support apparatus based on the patient. For example, the caregiver may choose to have the person-support apparatus alarm if the head section of the apparatus drops below a particular angle. Exit monitors may be set to a particular alarm level. Mattress operating parameters such as lateral rotation cycle times may also be set by the caregiver.

SUMMARY OF THE INVENTION

The present application discloses one or more of the features recited in the appended claims and/or the following features which, alone or in any combination, may comprise patentable subject matter:

According to the present disclosure, a person-support apparatus comprises a control system including, a processor, a receiver coupled to the processor, and a memory device. The receiver is configured to receive information corresponding to an occupant of the person-support apparatus. The memory device is coupled to the processor. The memory device includes default values for a plurality of operating parameters of the person-support apparatus. The memory device also includes instructions, that, when executed by the processor cause the processor to, operate the person-support apparatus utilizing the default values. The memory device still also includes instructions, that, when executed by the processor cause the processor to process information corresponding to an occupant of the person-support apparatus from the receiver to determine if an optimal value for an operating parameter is different from the default value. The memory device yet also includes instructions, that, when executed by the processor cause the processor to modify the operating parameter, if a change in an operating parameter is indicated. The memory device still yet also includes instructions, that, when executed by the processor cause the processor operate the person-support apparatus utilizing the modified operating parameter.

In some embodiments, the control system is in communication with a hospital network storing information that relates information regarding the information corresponding to an occupant of the person-support apparatus to an optimal value for an operating parameter of the person-support apparatus.

In some embodiments, the memory device includes instructions which, when executed by the processor, accesses a database to retrieve an optimal value for an operating parameter of the person-support apparatus that corresponds to the information corresponding an occupant of the person-support apparatus sensed by the receiver.

In some embodiments, the receiver comprises a sensor configured to detect a characteristic of an occupant of the person-support apparatus. The characteristic is utilized to determine an optimal value of an operating parameter of the person-support apparatus.

In some embodiments, the memory device includes instructions that, when executed by the processor, monitor the detected characteristic over time to establish additional information corresponding to the occupant of the person-support apparatus. In some embodiments, the characteristic corresponds to the mobility of the occupant. In some embodiments, the characteristic corresponds to the activity level of the patient. In some embodiments, the characteristic corresponds to the weight of the occupant.

In some embodiments, when the characteristic further corresponds to the mobility of the occupant, and the person-support apparatus further comprises an inflatable mattress, the operation of the inflatable mattress is modified based on the characteristic to set the operational parameters of the mattress to minimize the potential for skin damage to the occupant.

In some embodiments, the person-support apparatus further comprises a user interface and the receiver receives information regarding an occupant of the person-support apparatus from the user interface.

In some embodiments, the information corresponding to an occupant of the person-support apparatus includes a unique identifier of the occupant and the control system accesses the hospital network to acquire optimal operating parameters associated with the unique identifier stored on the hospital network.

In some embodiments, the person-support apparatus further includes a transmitter to transmit the modified operating parameter to a hospital network.

In some embodiments, the receiver receives information regarding a disease diagnosis of the occupant.

Further according to the present disclosure, a method of operating a person-support apparatus comprises the steps of operating the person-support apparatus according to a set of default operating parameters, processing information corresponding to an occupant of the person-support apparatus from the receiver to determine if an optimal value for an operating parameter is different from the default value, modifying a default operating parameter to an optimal value based on the information corresponding to the occupant of the person-support apparatus to create a modified operating parameter, and operating the person-support apparatus utilizing the modified operating parameter.

In some embodiments, the method further comprises the steps of communicating the information corresponding to an occupant of the person-support apparatus to a hospital network, receiving an optimal operating parameter for the person-support apparatus from the hospital network, and operating the person-support apparatus utilizing the optimal operating parameter.

In some embodiments, the method further comprises the step of processing information corresponding to an occupant of the person-support apparatus includes determining a unique identifier associated with the occupant of the person-support apparatus.

In some embodiments, the method further comprises the steps of transmitting the unique identifier to a hospital network, receiving an optimal operating parameter associated with the unique identifier from the hospital network, operating the person-support apparatus according to the optimal operating parameter.

In some embodiments, the optimal operating parameter is related to movement of the person-support apparatus.

In some embodiments, the optimal operating parameter is related to delivery of a therapy by the person-support apparatus.

In some embodiments, the optimal operating parameter is related to an alarm condition.

In some embodiments, the method further comprises the steps of determining that insufficient information is available to modify an operating parameter, outputting a prompt to a user interface requesting additional information, receiving additional information from the user interface, and processing the additional information to determine if an operating parameter should be modified.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
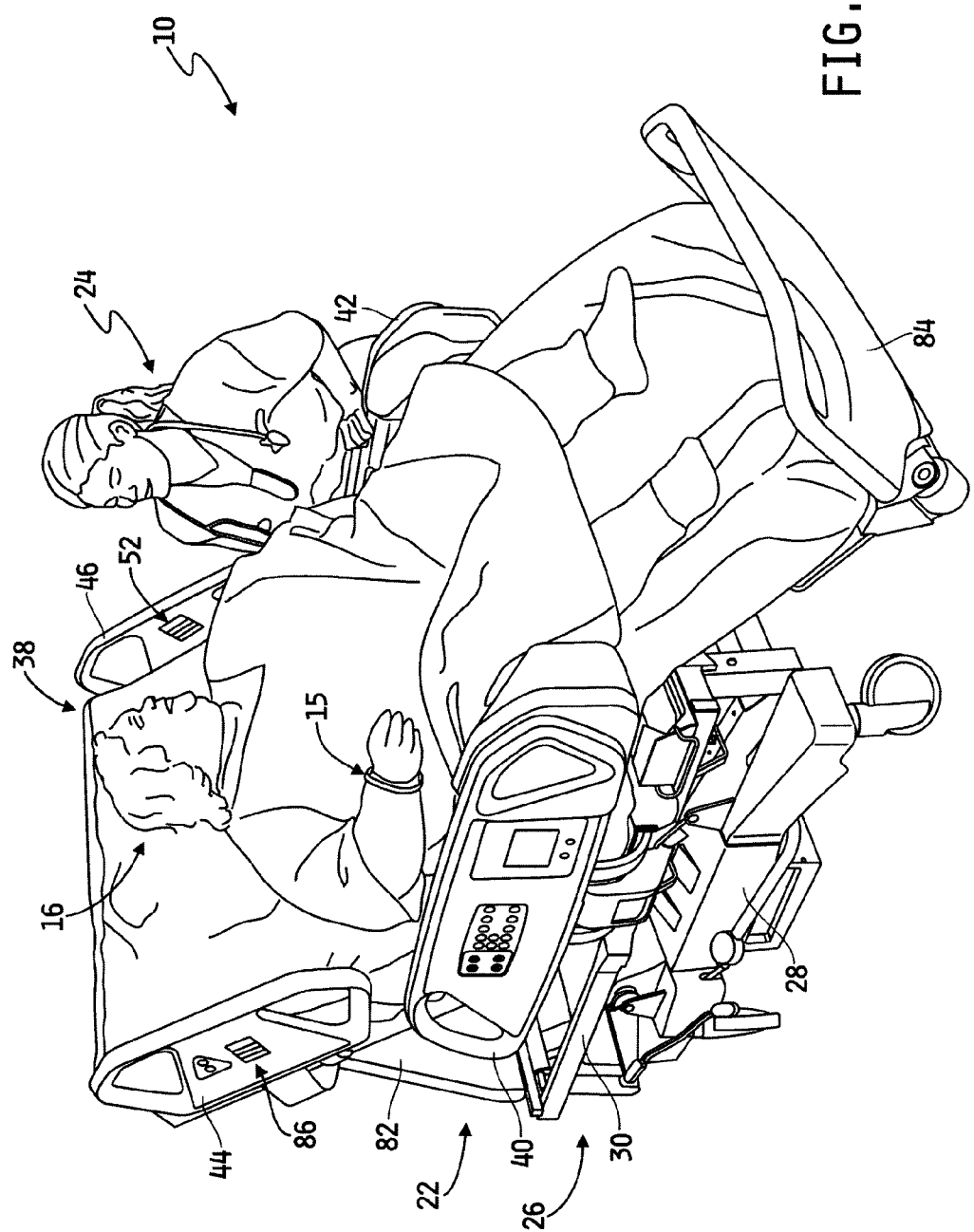
FIG. 1 is a perspective view of the person-support apparatus of the present disclosure.
Figure 2:
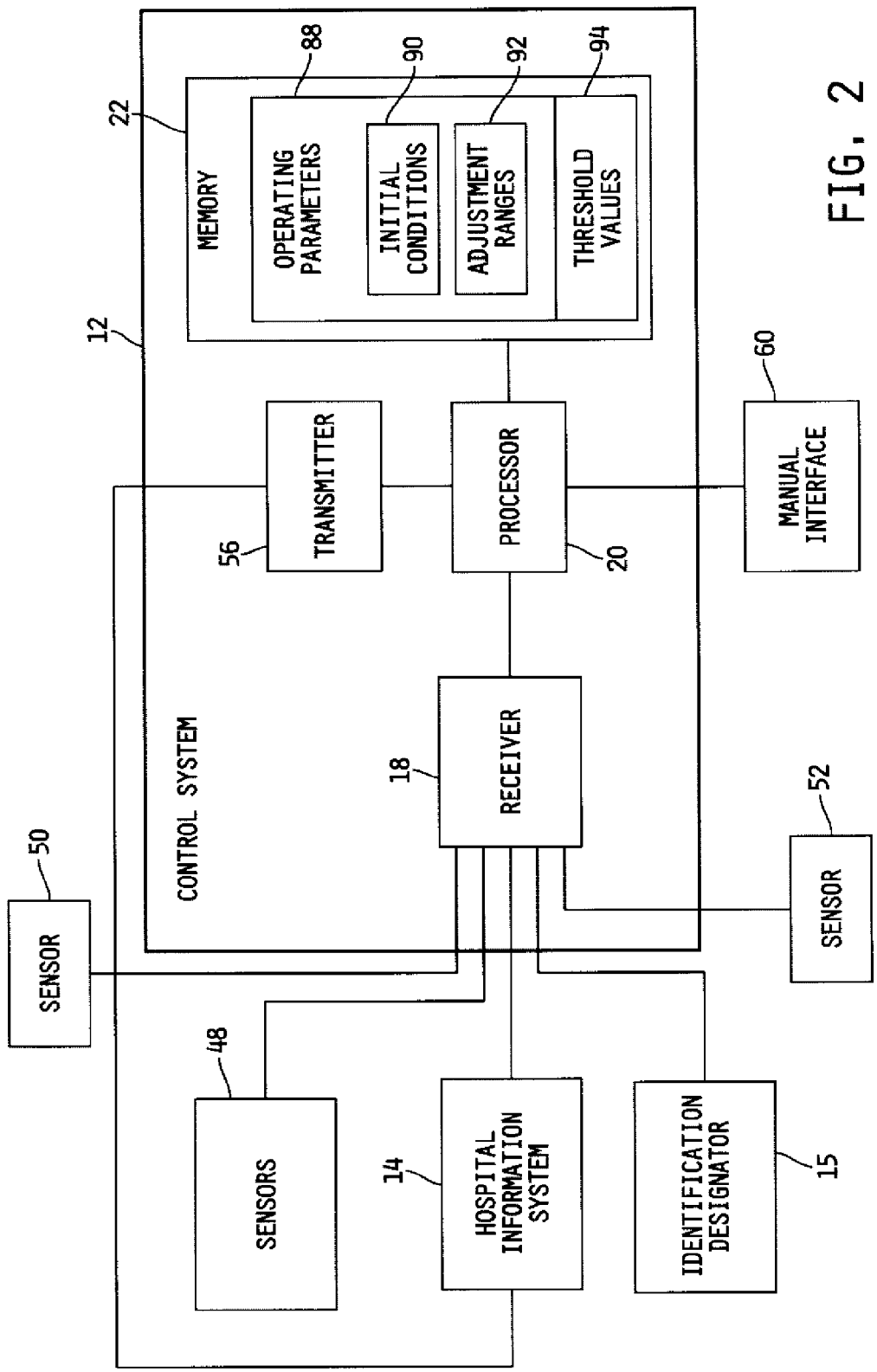
FIG. 2 is a diagrammatic representation of the control system of the person-support apparatus and components in communication with the control system.
Figure 3:
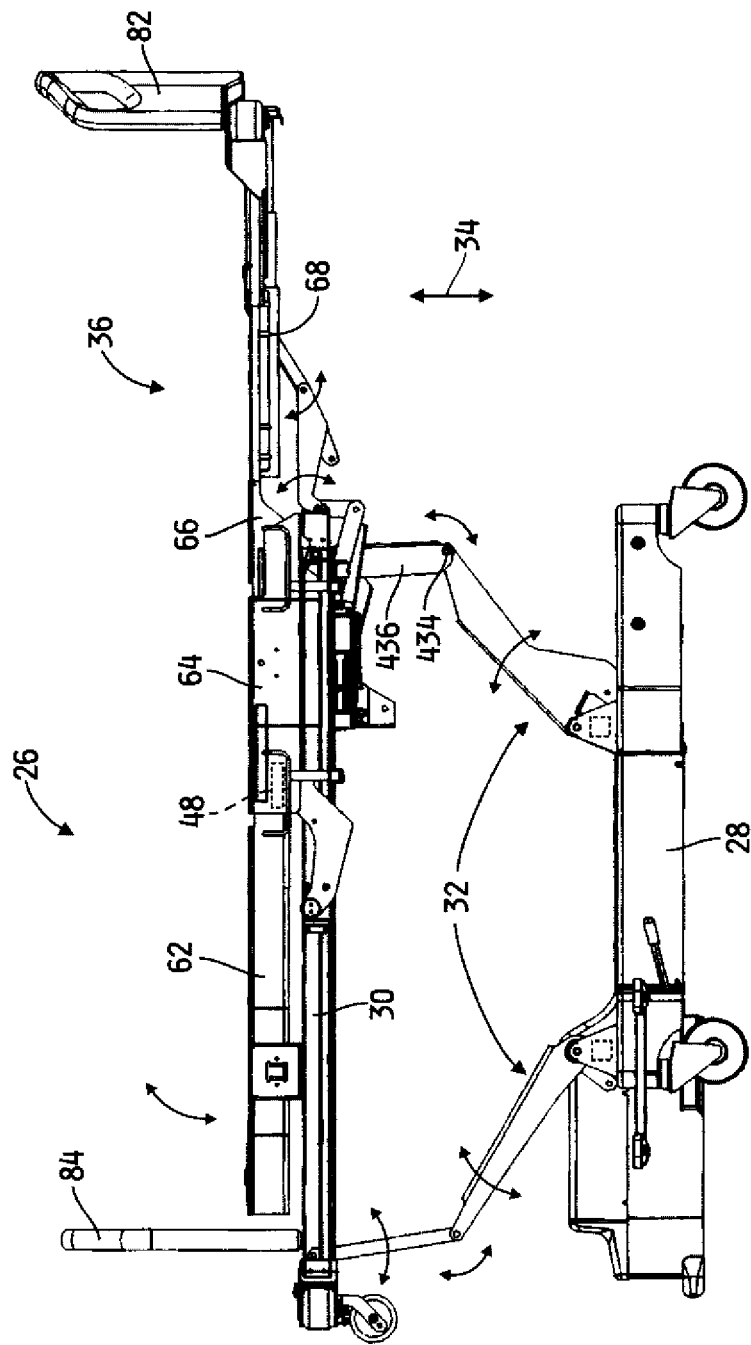
FIG. 3 is a side view of a frame of the person-support apparatus of FIG. 1, the person-support apparatus in a an elevated position.

A person-support apparatus shown in FIG. 1 is illustratively embodied as a hospital bed 10 and includes a control system 12 (shown diagrammatically in FIG. 2) that controls operation of the bed 10 and communicates with a hospital information system 14. The control system 12 collects information regarding an occupant of the bed 10, illustratively a patient 16. The control system 12 includes a receiver 18 for receiving information regarding a patient 16 in the bed 10. The receiver 18 is coupled to a processor 20. Referring again to FIG. 2, the processor 20 modifies operating parameters 88 of the bed 10. The operating parameters 88 of the bed 10 are stored in a memory device 22. The operating parameters 88 may be set to certain values based on the information regarding the patient 16. In the illustrative embodiment, the operating parameters 88 of the bed 10 include initial bed conditions 90 and allowable ranges of adjustment 92 available for selection by the patient 16 or a caregiver 24.

Figure 4:
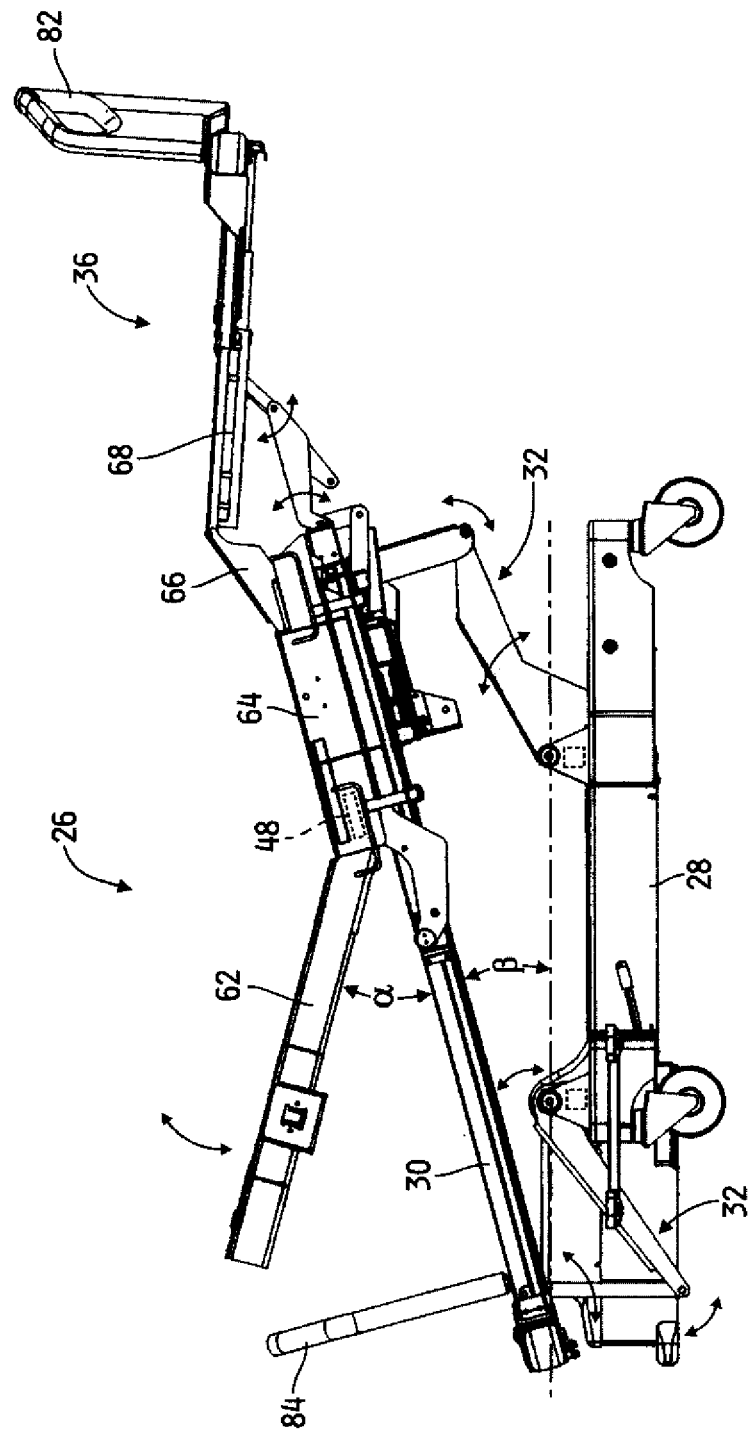
FIG. 4 is a side view of similar to FIG. 3, the frame of the person-support apparatus in a reclined configuration with a head section of the person-support apparatus raised.
Figure 5:
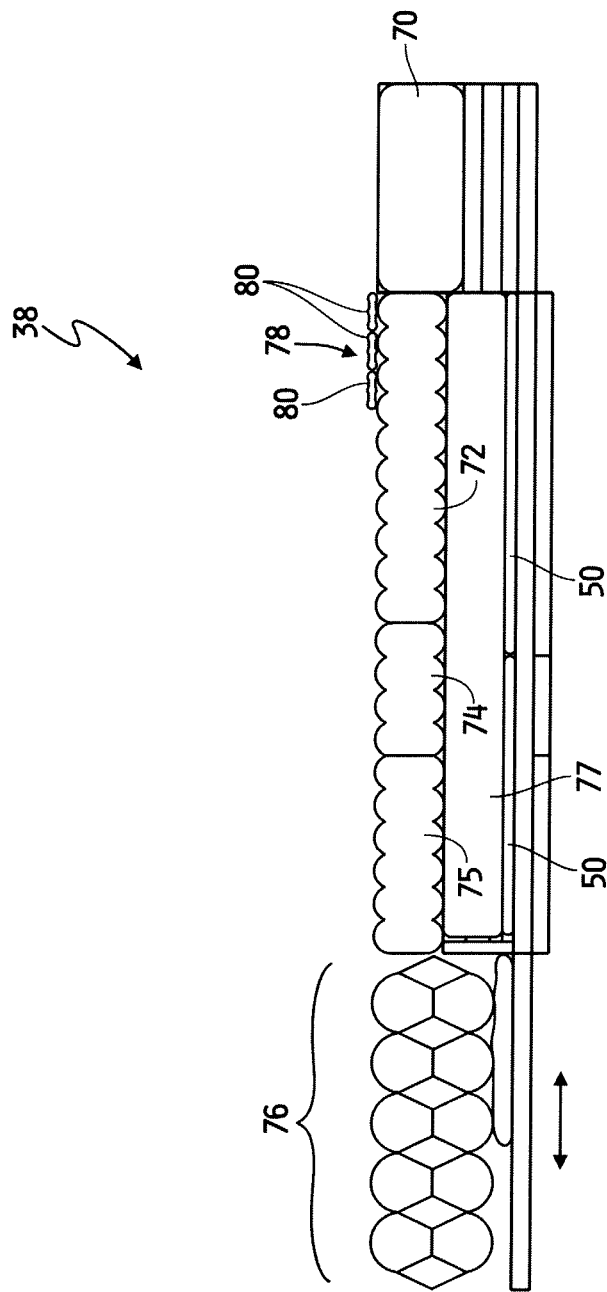
FIG. 5 is a diagrammatic side view of a portion of the mattress assembly with a cover removed.

Illustratively, the bed 10 includes a frame structure 26 having a lower frame 28 and an upper frame 30 which is movable relative the lower frame 28 as shown in FIG. 4. A lift system 32 is operable to raise and lower the upper frame 30 to the lower frame 28 as indicated by an arrow 34. A deck 36 is supported on upper frame 30 and is movable relative to the upper frame 30 to change the position of a patient 16 positioned on the bed 10. The bed 10 further includes a headboard 82, a footboard 84, siderails 40 and 42, and headrails 44 and 46.

The bed 10 includes a bed alarm 86 configured to sound under certain circumstances, such as when the patient 16 exits the bed 10, for example. In the illustrative embodiment, bed alarm 86 is coupled to the headrail 44. The bed alarm 86 may be enabled or disabled by the control system 12 based on certain operating conditions or input from a user.

A mattress 38 is supported on the deck 36. The mattress 38 includes a number of air bladders and foam components. Various controls for the bed 10 adjust the mattress 38 to provide various levels of firmness and therapies to a patient 16 supported on the mattress 38. For example, the mattress 38 is operable to provide percussion therapy to the patient 16. The mattress 38 is also configured to allow a caregiver 24 to deflate a portion of the mattress 38 to assist in moving a patient 16 such as for turning the patient 16 to change bed linens or to stiffen a portion of the mattress 38 to assist a patient 16 in exiting the bed 10. Additionally, the mattress 38 allows a patient 16 to select different levels of firmness to maximize comfort when the patient 16 is supported by the mattress 38. It should be understood that the mattress 38 is an illustrative embodiment and other mattresses having more or less features may be implemented within the scope of this disclosure.

The inflatable mattress 38, shown in FIG. 4, includes an inflatable head structure 70, an inflatable torso structure 72, an inflatable seat structure 74, an inflatable thigh structure 75, an inflatable foot structure 76, and a inflatable rotation structure 77. The inflatable rotation structure 77 underlies inflatable torso structure 72, inflatable seat structure 74, and inflatable thigh structure 76 and can be selectively deflated on lateral sides to rotate the torso of a patient supported on the mattress 38. Each of the inflatable mattress structures 70, 72, 74, 75, and 76 are made up of several inflatable bladders interconnected to form one inflatable unit. The foot structure 76 of the mattress 38 allows inflation of some bladders while other bladders are deflated to allow adjustment of the length of the foot section 76 to accommodate the height of the patient 16. Inflation of the bladders is controlled by the control system 12.

The inflatable torso structure 72 further includes a percussion and vibration assembly 78 located near the inflatable head structure 70. The percussion and vibration assembly 78 includes three percussion and vibration bladders 80. The percussion and vibration bladders 80 are independently and alternately inflatable to expand rapidly to impart a force to a chest area of a patient 16 supported on mattress 38. The percussive forces of the percussion and vibration assembly 78 reduce the potential for fluid to accumulate in the lungs of patient 16 by mechanically releasing secretions which accumulate and adhere to lung tissue. The percussion and vibration assembly 78 is controlled by control system 12.

The deck 36 illustratively includes a head section 62, a seat section 64, a thigh section 66, and a foot section 68. The sections 62, 64, 66, and 68 are articulated such that various sections of the deck 36 may be moved to raise, for example, the head, thighs, or feet of patient 16. Movement of the various deck sections 62, 64, 66, and 68 and the lift system 32 are controlled by the control system 12 as is known in the art.

As discussed above, the control system 12 includes the receiver 18 for receiving information regarding a patient 16 supported by bed 10. The receiver 18 accepts sensor information from three sensors 48, 50, 52 regarding patient 16. Illustratively, sensor 48 collects patient weight information; sensor 50 collects patient activity information; and sensor 52 collects patient blood oxygenation levels. The sensors 48, 50, and 52 are illustrative only. It should be understood that any of a number of patient characteristics may be collected by a number of sensors, with each of the characteristics being collected by the receiver 18 of the control system 12.

The receiver 18 is further configured to receive an identification designator 15 associated with the patient 16. The identification designator 15 is also called a unique identifier. Illustratively, the identification designator 15 is transmitted by a patient bracelet 54 containing a radio frequency identification (RFID) transmitter. In some embodiments, the identification designator 15 may be located on a patient chart. In other embodiments, a bar code on a patient bracelet may be read by a bar code scanner in communication with the receiver 18. It is within the scope of this disclosure for any of a number of articles that are uniquely associated with the patient 16 may provide the input to the receiver 18 of the control system 12. In some embodiments, the control system 12 also includes a transmitter 122 configured to transmit the identification designator 15 to the hospital information system 14. Upon receipt of an identification designator 15, the hospital information system 14 dispatches patient information resident in the hospital information system 14 to the receiver 18. In some embodiments, an RFID transmitter or bar code label may include specific information regarding the patient 16 such as age, sex, nutrition levels, or other information. In those embodiments, the bed 10 does not have to communicate with the hospital information system 14 but relies on the data input from the RFID transmitter or bar code for the information.

The control system 12 also includes a processor 20 coupled to the receiver 18. The processor 20 processes the patient information collected by the receiver 18 and determines operational factors for the bed 10 based on the patient information. The processor 20 is further modifies operating parameters 88 stored in a memory device 22 based on operational factors. As will be discussed below, the operating parameters 88 include limits on the operation of various functions of the bed 10.

The memory device 22 stores information including operating parameters 88 which include initial bed conditions 90 and allowable ranges of adjustment 92. Additionally, the memory device 22 stores threshold values 94 that are operational factor values defining the threshold for operation of the bed 10 based on the patient information. The threshold values 94 are also called optimal values. The threshold values 94 are compared with operational factors determined by the processor 20 to establish allowable ranges of adjustment 92.

The processor 20 is also coupled to a user interface 60, illustratively a touch-screen input/output device coupled to the siderail 40. The processor 20 prompts a user to enter patient information not provided by receiver 18 by displaying a request on user interface 60. The processor 20 receives additional patient information through input from the user interface 60. The user interface 60 also allows a caregiver 24 to update patient information to be utilized by processor 20 to over-ride previously entered information or to set narrower thresholds based on an assessment of the patient 16 by the caregiver 24.

The processor 20 is also coupled to a transmitter 122. The transmitter 122 periodically transmits information associated with the patient 16 such as patient characteristics and bed data to the hospital information system 14 for storage and to update patient records. Information associated with the patient 16 is then available later to other person-support apparatuses for incorporation into operational factors of the other person-support apparatuses if the patient is relocated. Illustratively, information associated with a patient 16 may include a manually input mobility factor from the assessment of the caregiver 24. The mobility factor is an indication of the ability of the patient to be ambulatory without assistance. This information is transmitted and logged by the hospital information system 14. If the patient 16 is later moved to a different hospital bed, the information collected about patient 16 is available for determination of operating parameters 88, such as bed-exit alarm parameters, without requiring duplicate manual input.

Figure 6:
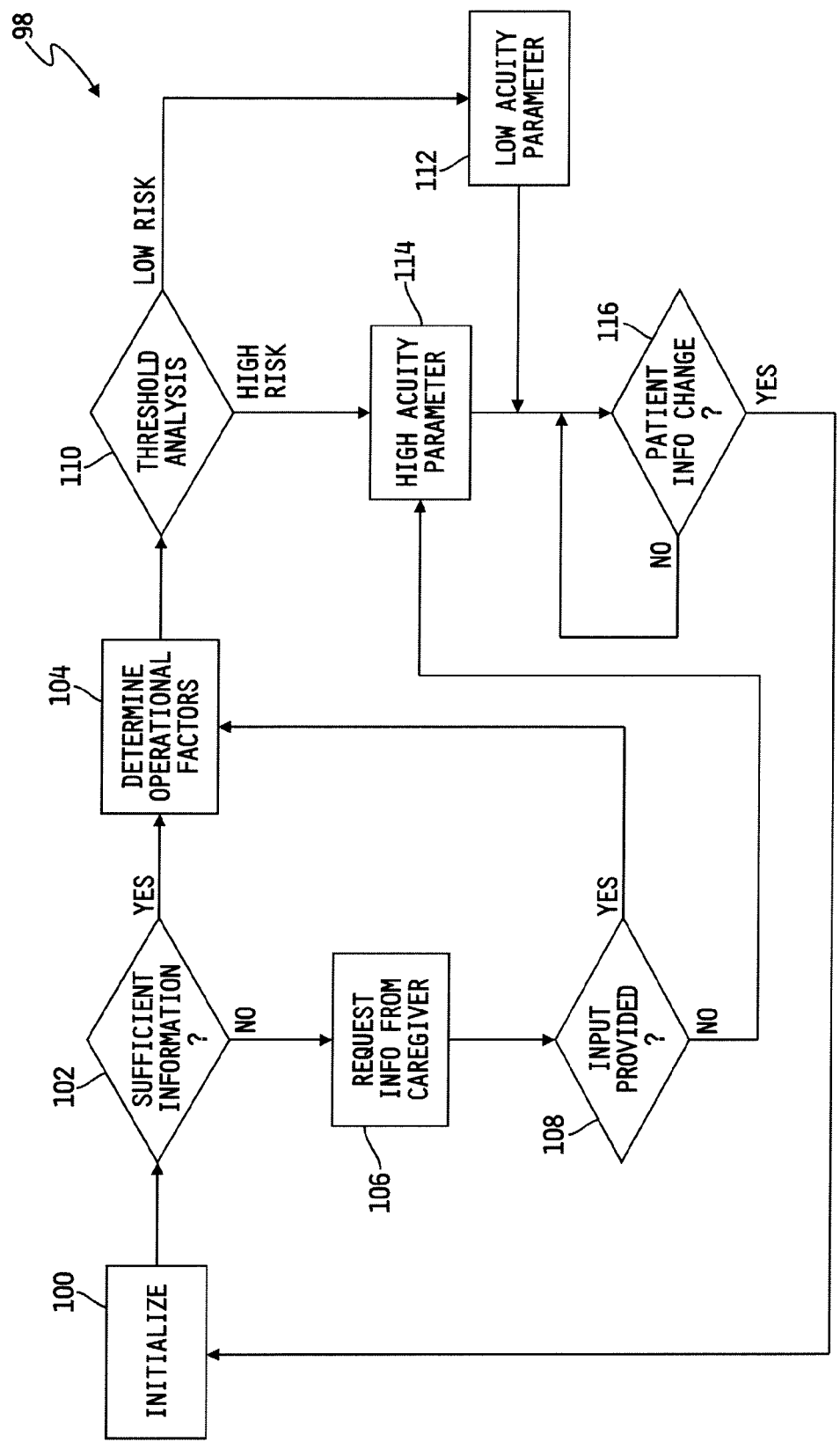
FIG. 6 is a diagrammatic representation of the processes performed by the processor included in the control system of the person-support apparatus.

A process 98 for setting operating parameters 88 of the bed 10, executed by the control system 12 is illustrated in FIG. 6. First, at process step 100, the processor 20 gathers the information provided by the receiver 18 to determine if the information available from sensors 48, 50, 52; identification designator 15; and hospital information system 14. A decision step 102 determines if the information provided is sufficient to determine all required operational factors of bed 10. If the information gathered by receiver 18 is sufficient, the process 98 proceeds to a process step 104 where the control system 12 determines a number of operational factors associated with the patient 16.

If the information is insufficient, the process proceeds to step 106 where the caregiver 24 is prompted to enter additional information into the user interface 60. At decision step 108, the algorithm determines if the requested information associated with the patient 16 is input by a caregiver 24. If it has, the process 98 proceeds to process step 104. If the requested information associated with the patient 16 is not supplied, the process 98 proceeds to process step 114 setting operating parameters 88 for a high risk patient. For example, if patient age is not available to the processor 20 and age is critical to determining an operational factor like the skin risk factor, the processor 20 will prompt the caregiver 24 with a request for patient age on the user interface 60. A caregiver 24 inputs patient age using the user interface 60. If patient age is not input, then the process 98 proceeds to process step 114.

Upon determination of operational factors at step 104, the process 98 proceeds to decision step 110 where the operational factors are compared to corresponding threshold values 94. If an operational factor is less than the corresponding threshold value 94, then process 98 proceeds to step 112 and the processor 20 modifies operating parameters 88 stored in the memory device 22 to a low acuity setting. If an operational factor is greater than the corresponding threshold value 94, then the process 98 proceed to step 114 and the processor 20 modifies operating parameters 88 stored in the memory device 22 to a high acuity setting.

For example, the processor 20 may determine a skin risk factor based on patient information including age, weight, sex, and patient activity level, among other things. If the skin risk factor is less than the high acuity threshold skin risk value, initial bed conditions 90 like firmness of the mattress 38 may be modified to optimize patient comfort rather than to minimize risk of skin pressure ulcers. Other operating parameters 88 may be modified to allow the patient 16 or the caregiver 24 to select firmer settings for the mattress 38 or increased seating angles of the deck 36 sections 62, 64, 66, and 68. The speed of deck 36 movement during adjustment may be modified as well.

Once the operational parameters have been established at process steps 112 and 114, the process 98 proceeds to decision step 116 where the processor 20 monitors for changes in patient information. If there has been no change in patient information, the operating parameters 88 are maintained and the monitoring process continues. If there has been a change in patient information, the process 98 returns to step 100 to evaluate the operating parameters 88 using the updated patient information.

In the illustrative embodiment, operational factors include a skin risk factor associated with risk of skin damage, specifically skin pressure ulcers; a fall risk factor associated with the risk of patient 16 falling out of the bed 10; and a pulmonary risk factor associated with the risk of fluid collection in the lungs of a patient. In the illustrative embodiment, the skin risk factor is determined with regard to modified Braden scale inputs. The fall risk factor is determined with regard to patient 16 age, sex, weight, and patient activity level, among other things. Additionally, pulmonary risk factor is determined with regard to patient age, sex, and blood oxygenation level, among other things. In addition, the factors may be modified by specific disease states for the patient. For example, if the patient is diagnosed with pneumonia, the pulmonary risk factor is increased. If the patient is diagnosed with diabetes, the risk factor for skin damage is increased. If the patient has dementia, the risk factor for patient falls is modified.

In the illustrative embodiment, the operating parameters 88 associated with mattress 38 that are modified by operational factor comparison to threshold values 94 include initial bed conditions 90 and allowable ranges of adjustment 92. The initial bed conditions 90 associated with mattress 38 include firmness/interface pressure of inflatable structures 70, 72, 74, 75, 76; the length of foot section 76; the operating parameters of pulmonary therapy. Allowable ranges of adjustment 92 associated with the mattress 38 include maximum and minimum firmness of inflatable structures 70, 72, 74, 75, 76 and the time interval of percussion and vibration therapy applied by assembly 78.

The initial bed conditions 90 associated with the deck 36 include relative angles of the deck sections 62, 64, 66, 68 and height of the upper frame 30 in relation to the lower frame 28. The allowable ranges of adjustment 92 associated with the deck 36 include maximum and minimum angles between the deck sections 62, 64, 66, 68; maximum and minimum height of the upper frame 30 relative to the lower frame 28; and the maximum speed of the deck 36 movement during adjustment. For example, the allowable ranges of adjustment 92 may limit the magnitude of an angle $\alpha$, shown in FIG. 4, between the upper frame 30 and the head section 62. The ranges of adjustment may also limit the magnitude of an of tilt of the upper frame 30 relative to horizontal as indicated by angle $\beta$ in FIG. 4. The ranges of adjustment 92 may also limit some combination of $\alpha$ and $\beta$.

An operating parameter 88 associated with the bed alarm 86 that is affected by operational factor comparison to threshold values 94 is the enablement of the bed alarm 86. In addition, the operation of a bed exit system may be enabled and set to a particular sensitivity level based on information associated with the patient.

While in the illustrative embodiment the receiver 18 is located on the bed 10, it is within the scope of this disclosure to position the receiver 18 proximate to, but not directly on the person-support apparatus. For example, in some embodiments the receiver 18 may be mounted to the head wall of the room in a position near to the bed 10. In other embodiments, the receiver may be mounted to an IV pole, a headboard 82 of the hospital bed 10, a footboard 64 of the hospital bed 10, the mattress 38 supported on the bed 10, or on some other structure of a room in which the bed 10 is located. For example, the receiver 18 may be positioned on the ceiling or on the floor proximate to the bed 10. In embodiments where the receiver 18 is spaced apart from the bed 10, the receiver 18 may be in wireless communication with the bed 10 utilizing an infrared (IR) emitter to communicate with an IR receiver mounted on the bed 10. In particular, this configuration may be employed when the bed 10 is docked to a particular location in a room thereby facilitating a line of sight between the infrared emitter and the infrared receiver because of the known location of the components on the bed 10. Utilizing the line of sight IR approach reduces the potential for information from multiple beds being confused by the receiver due to cross-communication between radio frequency signals.

Further, while in the illustrative embodiment the receiver 18 and the transmitter 122 are shown as separate components of the control system 12, it is contemplated that the receiver 18 and transmitter 122 may be combined into a receiver/transmitter unit as is well-known in the art.

While the bed alarm 86 is illustratively an audible signal, it is contemplated that the alarm signal may be visual. In some embodiments, the alarm signal may be transmitted by transmitter 122 to the hospital information system 14 for electronic dissemination to other notification devices, such as caregiver communication devices, for example.

Although certain illustrative embodiments have been described in detail above, variations and modifications exist within the scope and spirit of this disclosure as described and as defined in the following claims.

The invention claimed is:

1. A person-support apparatus comprising
a control system including, a processor, a receiver coupled to the processor, the receiver configured to receive information corresponding to an occupant of the person-support apparatus, and a memory device coupled to the processor, the memory device including a default value and allowable range of adjustment for each of a plurality of operating parameters of the person-support apparatus and including instructions, that, when executed by the processor cause the processor to, (i) operate the person-support apparatus such that an actual value of each of the plurality of operating parameters is maintained within the allowable range of adjustment of each of the plurality of default values, (ii) process information corresponding to an occupant of the person-support apparatus from the receiver to determine an optimal value and range of adjustment for an operating parameter, (iii) determine if the optimal value for an operating parameter is different from the default value, (iv) if a difference between the optimal value and the default value of an operating parameter is indicated, modify the default value and allowable range of adjustment of the operating parameter to the optimal value and range of adjustment respectively, and (v) operate the person-support apparatus such that the actual value of the operating parameter is maintained within the modified allowable range of adjustment of the operating parameter.

2. The person-support apparatus of claim 1, wherein the control system is in communication with a hospital network storing information that associates the information corresponding to an occupant of the person-support apparatus to an optimal value for an operating parameter of the person-support apparatus.

3. The person-support apparatus of claim 2, wherein the memory device includes instructions which, when executed by the processor, accesses the hospital network to retrieve an optimal value for an operating parameter of the person-support apparatus that corresponds to the information corresponding to an occupant of the person-support apparatus sensed by the receiver.

4. The person-support apparatus of claim 3, wherein the receiver comprises a sensor configured to detect a characteristic of an occupant of the person-support apparatus, the characteristic utilized to determine an optimal value of an operating parameter of the person-support apparatus.

5. The person-support apparatus of claim 4, wherein the memory device includes instructions that, when executed by the processor, monitor the characteristic over time to establish additional information corresponding to the occupant of the person-support apparatus.

6. The person-support apparatus of claim 5, wherein the characteristic corresponds to an activity level of the occupant.

7. The person-support apparatus of claim 5, wherein the characteristic corresponds to the weight of the occupant.

8. The person-support apparatus of claim 7, wherein the characteristic further corresponds to mobility of the occupant, the person-support apparatus further comprises an inflatable mattress, and the operation of the inflatable mattress is modified based on the characteristic to set the operational parameters of the inflatable mattress to minimize potential for skin damage to the occupant.

9. The person-support apparatus of claim 8, wherein the person-support apparatus further comprises a user interface and the receiver receives information regarding an occupant of the person-support apparatus from the user interface.

10. The person-support apparatus of claim 2, wherein the information corresponding to an occupant of the person-support apparatus includes a unique identifier of the occupant and wherein the control system accesses the hospital network to acquire optimal operating parameters associated with the unique identifier stored on the hospital network.

11. The person-support apparatus of claim 1, wherein the person-support apparatus further includes a transmitter to transmit the modified operating parameter to a hospital network.

12. The person-support apparatus of claim 1, wherein the receiver receives information regarding a disease diagnosis of the occupant.

13. A method of operating a person-support apparatus, the method comprising the steps of:
operating the person-support apparatus according to a default value of a number of operating parameters,
processing information corresponding to an occupant of the person-support apparatus,
determining an optimal value for an operating parameter based on the information corresponding to the occupant,
determining if the optimal value for the operating parameter is different from the default value,
if a difference between the optimal value and the default value of an operating parameter is indicated, modifying the default value of the operating parameter to the optimal value to create a modified value for the operating parameter, and
operating the person-support apparatus within an allowable range of adjustment of the modified value for the operating parameter.

14. The method of claim 13, further comprising the steps of communicating the information corresponding to an occupant of the person-support apparatus to a hospital network,
receiving an optimal value for an operating parameter for the person-support apparatus from the hospital network, and
operating the person-support apparatus utilizing the optimal value for the operating parameter.

15. The method of claim 13, wherein the step of processing information corresponding to an occupant of the person-support apparatus includes determining a unique identifier associated with the occupant of the person-support apparatus.

16. The method of claim 15, further comprising the steps of transmitting the unique identifier to a hospital network,
receiving an optimal value for an operating parameter associated with the unique identifier from the hospital network,
operating the person-support apparatus according to the optimal value for the operating parameter.

17. The method of claim 16, wherein the optimal value for an operating parameter is related to movement of the person-support apparatus.

18. The method of claim 16, wherein the optimal value for the operating parameter is related to delivery of a therapy by the person-support apparatus.

19. The method of claim 16, wherein the optimal value for the operating parameter is related to an alarm condition.

20. The method of claim 13, further comprising the steps of determining that insufficient information is available to determine the optimal value for an operating parameter,
outputting a prompt to a user interface requesting additional information,
receiving additional information from the user interface, and
processing the additional information to determine the optimal value for an operating parameter.

21. A person-support apparatus comprising
a control system including, a processor, a receiver coupled to the processor, the receiver configured to receive information corresponding to an occupant of the person-support apparatus, and a memory device coupled to the processor, the memory device including a default value and allowable range of adjustment for each of a plurality of operating parameters of the person-support apparatus and including instructions, that, when executed by the processor cause the processor to, (i) operate the person-support apparatus such that an actual value of each of the plurality of operating parameters is maintained within the allowable range of adjustment of each of the plurality of default values, (ii) process information corresponding to an occupant of the person-support apparatus from the receiver to determine an optimal value and range of adjustment for an operating parameter, (iii) determine if the optimal value for an operating parameter is different from the default value, (iv) if a difference between the optimal value and the default value of an operating parameter is indicated, modify the default value and allowable range of adjustment of the operating parameter to the optimal value and range of adjustment respectively, and (v) operate the person-support apparatus such that the actual value of the operating parameter is maintained within the modified allowable range of adjustment of the operating parameter,
wherein the receiver comprises a sensor configured to detect a characteristic of an occupant of the person-support apparatus, the characteristic utilized to determine an optimal value of an operating parameter of the person-support apparatus, and wherein the characteristic further corresponds to mobility of the occupant, the person-support apparatus further comprises an inflatable mattress, and the operation of the inflatable mattress is modified based on the characteristic to set the operational parameters of the inflatable mattress to minimize potential for skin damage to the occupant.

22. The person-support apparatus of claim 21, wherein the memory device includes instructions that, when executed by the processor, monitor the characteristic over time to establish additional information corresponding to the occupant of the person-support apparatus.

23. A person-support apparatus comprising a control system including, a processor, a sensor coupled to the processor, the sensor configured to detect a characteristic of an occupant of the person-support apparatus, and a memory device coupled to the processor, the memory device including a default value and allowable range of adjustment for each of a plurality of operating parameters of the person-support apparatus and including instructions, that, when executed by the processor cause the processor to, (i) operate the person-support apparatus such that an actual value of each of the plurality of operating parameters is maintained within the allowable range of adjustment of each of the plurality of default values, (ii) process information corresponding to an occupant of the person-support apparatus from the receiver to determine an optimal value and range of adjustment for an operating parameter, (iii) determine if the optimal value for an operating parameter is different from the default value, (iv) if a difference between the optimal value and the default value of an operating parameter is indicated, modify the default value and allowable range of adjustment of the operating parameter to the optimal value and range of adjustment respectively, and (v) operate the person-support apparatus such that the actual value of the operating parameter is maintained within the modified allowable range of adjustment of the operating parameter.

24. The person-support apparatus of claim 23, wherein the characteristic further corresponds to mobility of the occupant.

25. The person-support apparatus of claim 24, further comprising an inflatable mattress, and the operation of the inflatable mattress is modified based on the characteristic to set the operational parameters of the inflatable mattress to minimize potential for skin damage to the occupant.

26. A method of operating a person-support apparatus, the method comprising the steps of:

operating the person-support apparatus according to a default value of a number of operating parameters, processing information corresponding to an occupant of the person-support apparatus, determining an optimal value for an operating parameter based on the information corresponding to the occupant, determining if the optimal value for the operating parameter is different from the default value without input from a user, if a difference between the optimal value and the default value of an operating parameter is indicated, modifying the default value of the operating parameter to the optimal value to create a modified value for the operating parameter without input from a user, and operating the person-support apparatus within an allowable range of adjustment of the modified value for the operating parameter without input from a user.

* * * * *